(12) United States Patent
Findlay et al.

(10) Patent No.: US 6,812,356 B2
(45) Date of Patent: Nov. 2, 2004

(54) CONVERSION 9-DIHYDRO-13-ACETYLBACCATIN III INTO 10-DEACETYLBACCATIN III

(76) Inventors: John Findlay, c/o Department of Chemistry, University of New Brunswick, 3 Bailey Drive, P.O. Box 4400, Fredericton, New Brunswick (CA), E3B 5A3; Ghislain Deslongchamps, c/o Department of Chemistry, University of New Brunswick, 3 Bailey Drive, P.O. Box 4400, Fredericton, New Brunswick (CA), E3B 5A3; Guoqiang Li, c/o Diagnostic Chemicals Limited, West Royalty Industrial Park, Charlestown, Prince Edward Island (CA), C1E 2A6

( * ) Notice: Subject to any disclaimer, the term of this patent is extended or adjusted under 35 U.S.C. 154(b) by 28 days.

(21) Appl. No.: 10/254,972

(22) Filed: Sep. 26, 2002

(65) Prior Publication Data

US 2004/0063976 A1 Apr. 1, 2004

(51) Int. Cl.$^7$ .............................................. C07D 305/14
(52) U.S. Cl. ...................................... 549/510; 549/511
(58) Field of Search .................................. 549/510, 511

(56) References Cited

U.S. PATENT DOCUMENTS 6,576,777 B2 * 6/2003 Zamir et al. ................ 549/510

2002/0128498 A1    9/2002   Zamir et al.

FOREIGN PATENT DOCUMENTS

| CA | 2 188 190 A | 4/1998 |
| WO | WO 98 50378 A | 11/1998 |
| WO | WO 99 54322 A | 10/1999 |
| WO | WO 01 70717 A | 9/2001 |

OTHER PUBLICATIONS

Corey, EJ: "Chromium trioxide–3, 5–dimethylpyrazole complex as a reagent for oxidation of alcohols to carbonyl compounds", Tetrahedron Letters, vol. 45, 1973, pp. 4499–4501.

* cited by examiner

Primary Examiner—Ba K. Trinh
(74) Attorney, Agent, or Firm—Stikeman Elliott LLP

(57) ABSTRACT

9-dihydro-13-acetylbaccatin III, one of the chemicals obtained from *Taxus canadensis* is used to produce, inter alia, 10-decetylbaccatin III, a useful intermediate for the preparation of paclitaxel and analogues thereof The 9-dihydro-13-acetylbaccatin III is converted into the 10-deacetylbaccatin III by a simple three step process involving (a) replacement of the C-7 hydroxyl group of tho 9-dihydro compound with a protecting group, (b) the oxidizing of the C-7 protected compound to produce a C-9 ketone, and (c) the deprotecting of the C-9 ketone to produce 10-deacetylbaccatin III.

8 Claims, No Drawings

CONVERSION 9-DIHYDRO-13-ACETYLBACCATIN III INTO 10-DEACETYLBACCATIN III

BACKGROUND OF THE INVENTION

1. Field of the Invention

This invention relates to a method of converting 9-dihydro-13-acetylbaccatin III to 10-deacetylbaccatin III.

2. Discussion of the Prior Art

Many taxanes, e.g. paclitaxel and docetaxol are being aggressively studied and tested for use as cancer treating agents. As described in many publications such as Canadian Patent Application No. 2,188,190, published Apr. 18, 1998 in the name of Zamir et al, which is incorporated herein by reference, the taxanes are active in various tumor systems. Taxanes are substances occurring naturally in yew trees such as *Taxus canadensis*, which is common in Eastern Canada and the United States. One of the chemicals extracted from the needles of *Taxus canadensis* is 9-dihydro-13-acetylbaccatin III, which is used to produce, inter alia, 10-deacetylbaccatin III—a useful intermediate for the preparation of paclitaxel and analogues thereof.

Various methods of converting 9-dihydro-13-acetylbaccatin III into 10-deacetylbaccatin III have been proposed (see, for example the above mentioned CA 2,188, 190). However, it has been found that such methods result in poor yields of finished product. Thus, a need still exists for an efficient method for converting 9-dihydro-13 acetylbaccatin III to 10-deacetylbaccatin III (DAB III).

GENERAL DESCRIPTION OF THE INVENTION

The object of the present invention is to meet the above defined need by providing a relatively efficient method of converting 9-dihydro-13-acetylbaccatin III to DAB III.

Accordingly, the invention relates to a method of converting 9-dihydro-13-acetylbaccatin III into 10-deacetylbaccatin III comprising the steps of (a) protecting the C-7 group of 9-dihydro-13-acetylbaccatin III by replacing the C-7 hydroxyl group with a protecting group;

(b) oxidizing the C-9 hydroxyl group in the resulting product to produce a C-9 ketone; and (c) deprotecting the C-9 ketone to form 10-deacetylbaccatin III.

DESCRIPTION OF THE PREFERRED EMBODIMENT

General Procedure

The first step in the method of the present invention involves the dissolving of 9-dihydro-13-acetylbaccatin III in dry solvent such as $CH_2Cl_2$, $CHCl_3$, THF, $Et_2O$ or Bz. A dry base, e.g. pyridine, TEA or $NaHCO_3$ and/or a catalytic amount of p-N,N-dimethylaminopyridine (DMAP) is added to the solution, followed by 1–6 equivalents of a protecting reagent (TMSCl, TESCl or $Ac_2O$) at a temperature of between room temperature and −78° C. The mixture is stirred continuously for 0.5–6 hours before being quenched by the addition of water. The mixture is poured into ethyl acetate and washed sequentially with dilute acid, water and brine, and dried over magnesium sulfate. The solution is evaporated under vacuum to give a crude solid (7-OH protected-9-baccatin III up to 91% yield)

A 3,5-disubstituted pyrazole such as 3,5-dimethyl-pyrazole is added to a suspension of metal oxide, e g. chromium trioxide (2–20 equivalents) in a solvent. Suitable solvents include $CH_2Cl_2$, $CHCl_3$, THF, $Et_2O$ and Bz. The mixture is stirred at room temperature for at least 15 minutes. A 7-OH protected 9-dihydro-13-acetylbaccatin III in the same solvent is added to the solution in one portion, and the mixture is stirred for 0.5 hour to one week to produce a C-9 ketone in up to 90% yield.

The C-9 ketone is dissolved in a suitable organic solvent such as an alcohol, an ether, $CH_2Cl_2$ or $CHCl_3$ with or without water, and reacted with an acid, a base, or a strong nucleophile, such as a bicarbonate, a carbonate, ammonia, an amine, a hydrazine, a hydroxide, a hydroperoxide or an alyllithium. The reaction mixture thus produced is stirred at a controlled temperature (0° C. to solvent reflux). The reaction is monitored by thin-layer chromatography until it has progressed satisfactorily. Routine liquid extraction is performed followed by solvent evaporation to produce crude 10-deacetylbaccatin III in up to 85% yield.

The reaction scheme for the above described general procedure is as follows

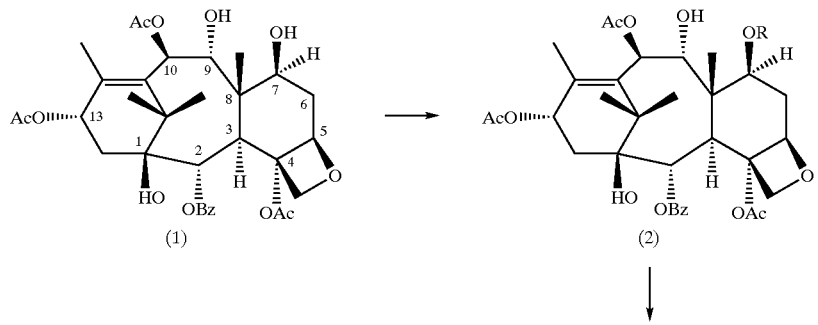

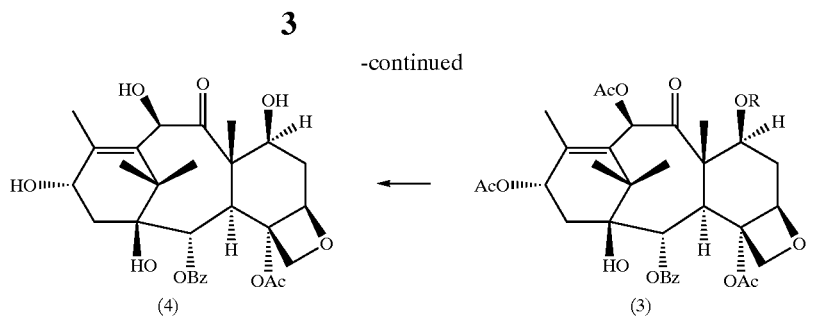

Several experiments were carried out using a variety of reagents to produce 7-OH protected-9-baccatin III with different protecting groups in the 7-position. The results of the experiments are listed in Tables 1 and 2 (for the sake of simplicity, all tables are found at the end of this description).

Additional experiments were conducted in which R in the above formulae was an acetyl group.

In accordance with a preferred embodiment of the invention, R in the above formula is an acetyl group. The reaction scheme for the preferred embodiment is as follows

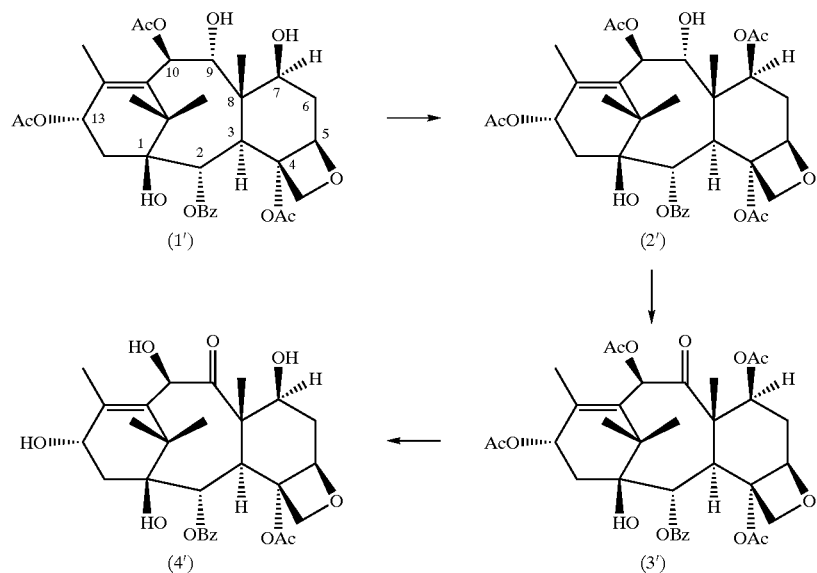

EXAMPLES

Selective Protection of 7-hydroxyl Group of 9-dihydro-13-acetylbaccatin III

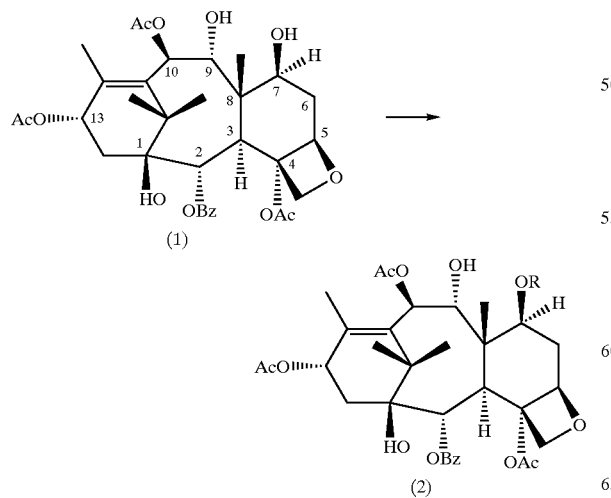

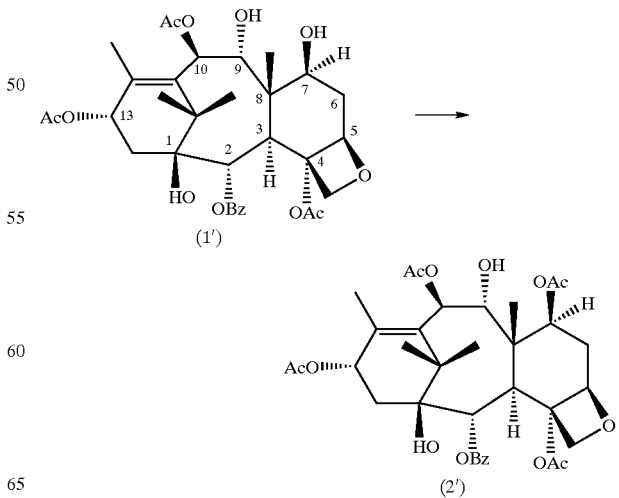

In the method of producing 9-dihydro-7,13-diacetylbaccatin III, 9-dihydro-13-acetylbaccatin III (0 1 mmole) was dissolved in 2.5 mL of dry methylene chloride and cooled to −23° C. using a slurry of $CCl_4$ and liquid nitrogen. 0.6 mmole of dry pyridine and a catalytic amount of DMAP (5% in mole) were added to the mixture followed by 0.3 mmole of acetic anhydride. The mixture was stirred for 1 5 h and then the reaction was quenched by the addition of 5.0 mL of water. The mixture was poured into 25 mL of ethyl acetate and washed sequentially with 15 mL of 1% HCl, 15 mL water and mL brine, and dried over $MgSO_4$. The solution was evaporated under vacuum and gave a crude solid (95% yield, 91% 9-dihydro-7,13-diacetylbaccatin III). The details and results of similar experiments are listed in Table 2.

Oxidation of the Protected 9-dihydro-13 acetylbaccatin III

Details of experiments using a variety of reagents and conditions are listed in Table 3

Subsequent oxidation experiments (which are listed as Examples 45 to 49 in Table 4) were conducted using 9-dihydro-7,13-diacetylbaccatin III as the starting material.

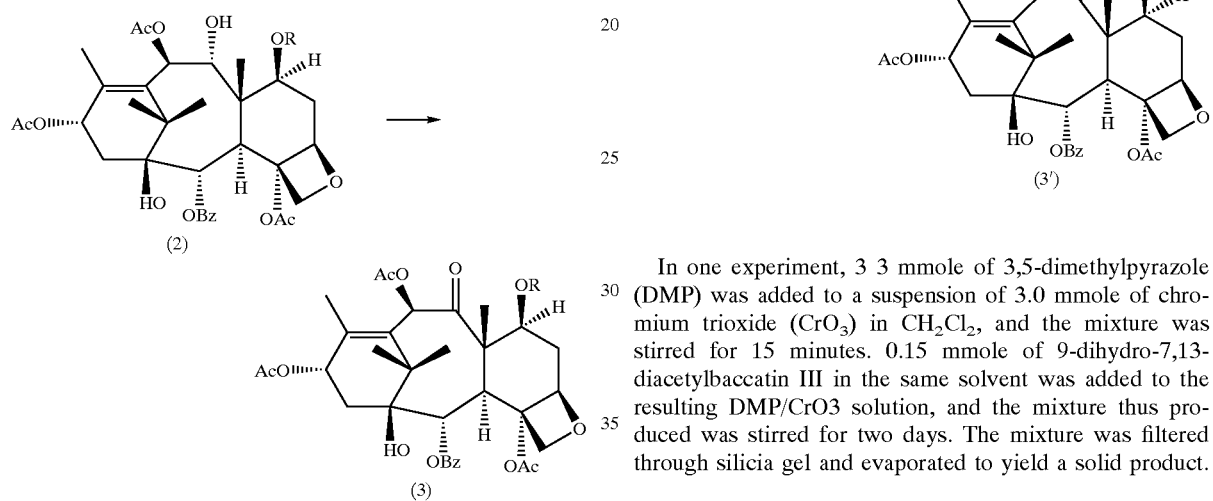

In one experiment, 3 3 mmole of 3,5-dimethylpyrazole (DMP) was added to a suspension of 3.0 mmole of chromium trioxide ($CrO_3$) in $CH_2Cl_2$, and the mixture was stirred for 15 minutes. 0.15 mmole of 9-dihydro-7,13-diacetylbaccatin III in the same solvent was added to the resulting DMP/CrO3 solution, and the mixture thus produced was stirred for two days. The mixture was filtered through silicia gel and evaporated to yield a solid product.

Details of the experiments (Examples 45 to 49) are found in Table 4.

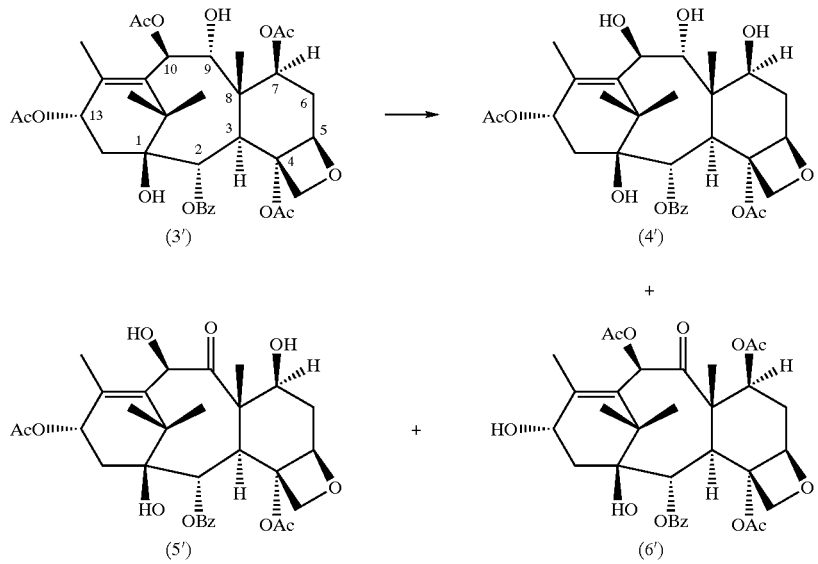

Several experiments were conducted using various reagents and conditions. Details of the experiments are listed in Examples 50 to 75 in Tables 5 and 6.

Additional experiments were carried out using 7,13-diacetylbaccatin III as the starting material to produce the desired product, DAB-III. In a specific reaction of this type, a solution of 4.5 mg (0.00675 mmole) of 7,13-diacetylbaccatin III in 0.08 mL of 95% ethanol was cooled to 7° C. 0 08 ml of hydrazine hydrate was added to the solution, which was then kept at 7° C. for 141 5 hours. The resulting mixture was diluted with ethyl acetate, and then washed sequentially with saturated aqueous ammonium chloride, water and brine. The organic layer was dried over $MgSO_4$, filtered and evaporated in vacuo to yield 4.2 mg of crude product. NMR spectroscopy revealed that the product consisted mainly of 10-deacetylbaccatin III plus trace amounts of by-products. The conditions and results of the hydrazine-based hydrolysis experiments are listed in Examples 76 to 112 in Table 6.

From the foregoing, and in particular from the specific examples, it is readily apparent that the preferred method of converting 9-dihydro-13-acetylbaccatin III into 10-deacetylbaccatin III involves the steps of:

(a) protecting the C-7 position of the 9-dihydro-13-acetylbaccatin III with an acetyl group using acetic anydride in the presence of a base and DMAP to produce 9-dihydro-7,13-diacetylbaccatin III, (b) oxidizing the 9-dihydro-7,13-diacetylbaccatin III using $CrO_3$/DMP to produce 7,13-diacetylbaccatin III, (the choice of oxidant here is important to success),and (c) replacing the C-7, C-10 and C-13 OAc groups in the 7,13-diacetylbaccatin III with OH groups using hydrazine hydrate.

TABLE 1

| Example | Reagents and Conditions | | Yield |
|---|---|---|---|
| 1 | R = TES | TES-Cl (7.5 eq), pyr, $CH_2Cl_2$, RT, 24h | 43% |
| 2 | R = TES | TES-Cl (5 eq), TEA, $CH_2Cl_2$, RT, 2.5H | |
| 3 | R = TES | TES-Cl (3 eq), pyr, $CH_2Cl_2$, RT, 24h | |
| 4 | R = TES | TES-Cl (5 eq), TEA, $CH_2Cl_2$, −89° C., 4h | >90% |
| 5 | R = TES | TES-Cl (5 eq), TEA, $CH_2Cl_2$, −89° C., 2.5h | >95% |
| 6 | R = TES | TES-Cl (5 eq), TEA, $CH_2Cl_2$, −89° C. | >97% |
| 7 | R = Ac | $Ac_2O$ (10 eq), TEA, DMAP, $CH_2Cl_2$, −89° C. | >51% |
| 8 | R = CBz | $Cl_2CBz$ (4 eq), TEA, $CH_2Cl_2$, RT, 20h | a |
| 9 | R = $CO_2Me$ | MeOCOCl (2 eq), DMAP, TEA, $CH_2Cl_2$, RT, 24h | b |
| 10 | R = $CO_2Me$ | MeOCOCl (5 eq), TMP, $CH_2Cl_2$, RT, 24h | c |
| 11 | R = $CO_2CF_3$ | $(CF_3CO)_2O$ (5 eq), Pyr, RT, 24h | d |
| 12 | R = Ac | $Ac_2O$ (5 eq), Pyr, DMP, $CH_2Cl_2$, 0° C., 6h | >50% |
| 13 | R = $CO_2CCl_3$ | $CCl_3COCl$ (2 eq), TEA, $CH_2Cl_2$, 0° C., 24 h | e | a: no reaction
b: formed carbonate with 9-OH
c: major product 7,9-carbonate
d: decomposed
e: low yield

TABLE 2

| Example | 9-DHB (mmole) | $Ac_2O$ (mmole) | Solvents (mL) | DMAP | Temperature (° C.) | Reaction Time | Yield (%) | 7-Acetyl (%) |
|---|---|---|---|---|---|---|---|---|
| 14 | 0.25 | 0.375 | Pyr (5) | Yes | 0-RT | 20 | 55 | 76 |
| 15 | 0.1 | 0.3 | Pyr (2.5) | Yes | 0 | 1:20' | >95 | 78–82 |
| 16 | 0.1 | 0.3 | Pyr (2.5) | Yes | RT | 1:20' | >95 | 55–69 |
| 17 | 0.1 | 0.3 | TEA (2), THF (1) | Yes | 0 | 2 | >95 | 42–62 |
| 18 | 0.1 | 0.3 | Pyr (2.5) | Yes | 0 | 53' | >90 | 71–83 |
| 19 | 0.1 | 0.3 | Pyr (2.5), THF (1) | Yes | −23 | 3 | >92 | 84–92 |
| 20 | 0.1 | 0.3 | Pyr (1), DCM (2) | Yes | −23 | 1.5 | >97 | 85–89 |
| 21 | 0.1 | 0.3 | Pyr (1), DCM (2) | Yes | −43 | 1.5 | >93 | 85–95 |
| 22 | 0.1 | 0.3 | Pyr (6 eq), DCM (2.5) | Yes | −23 | 1.5 | >95 | 87–94 |
| 23 | 0.1 | 0.3 | TEA (6 eq), DCM (2.5) | Yes | −23 | 1.5 | >96 | 79 |

TABLE 3

| Example | Reagents and Conditions | | Yield |
|---|---|---|---|
| 24 | R = TES | $CrO_3Pyr_2$(12 eq), $CH_2Cl_2$, RT | a |
| 25 | R = TES | DMSO (4.8 eq), $(COCl)_2$ (2.2 eq), TEA (5 eq), $CH_2Cl_2$ | a |
| 26 | R = TES | DMSO (4.8 eq), $(COCl)_2$ (2.2 eq), TEA (5 eq), $CH_2CL_2$ | a |
| 27 | R = TES | DMSO (9.6 eq), $(COCl)_2$ (4.4 eq), TEA (10 eq), $CH_2CL_2$ | a |
| 28 | R = TES | DMSO (2.2 eq), $(COCl)_2$ (2.2 eq), TEA (5 eq), $CH_2CL_2$ | a |
| 29 | R = TES | DMSO (2.4 eq), $(COCl)_2$ (2.2 eq), TEA (5 eq), $CH_2CL_2$ | a |
| 30 | R = TES | DMSO (9.6 eq), $(COCl)_2$ (4.4 eq), TEA (10 eq), $CH_2CL_2$ | a |
| 31 | R = TES | DMSO (9.6 eq), $(COCl)_2$ (4.4 eq), TEA (10 eq), $CH_2CL_2$ | a |
| 32 | R = TES | DMSO (5 eq), $(COCl)_2$ (5.5 eq), TEA (6 eq), $CH_2CL_2$ | a |
| 33 | R = TES | DMSO (5.5 eq), $(COCl)_2$ (5 eq), TEA (6 eq), $CH_2CL_2$ | a |
| 34 | R = TES | $NaClO_2$, $NaH_2PO_4$, 1-BuOH, 2-Methyl-2-butene | b |

TABLE 3-continued

| Example | Reagents and Conditions | | Yield |
|---|---|---|---|
| 35 | R = TES | Al(OPr-)$_3$, Acetone, C$_8$F$_5$OH | b |
| 36 | R = TES | CrO$_3$ (8 eq), 3.5-DMP (6.3 eq), CH$_2$Cl$_2$ | b |
| 37 | R = TES | Br$_2$, HMPA, CH$_2$Cl$_2$ | |
| 38 | R = TES | Ca(OCl)$_2$ HOAc | b |
| 39 | R = Ac | CrO$_3$ (10 eq), 3,5-DMP (12 eq), CH$_2$Cl$_2$ | 85% |
| 40 | R = Ac | DMSO (12 eq), (COCl)$_2$ (10 eq), TEA (20 eq), CH$_2$Cl$_2$ | b |
| 41 | R = Ac | CrO$_3$-Pyr$_3$ (6 eq), CH$_2$Cl$_2$, RT, 2 days | b |
| 42 | R = TES | CrO$_3$ (10 eq), 1H-Tetrazole (10.2 eq), CH$_2$Cl$_2$ | a |
| 43 | R = TES | CrO$_3$ (10 eq), 2-(1H)-Pyridone (10.2 eq), CH$_2$Cl$_2$ | b |
| 44 | A = Ac | MnO$_2$ (20 eq), CH$_2$Cl$_2$, RT, 2 days | b | a: decomposed b: no reaction

TABLE 4

| Example | Reagents and Conditions | Weight of SM (mg) | Yield % |
|---|---|---|---|
| 45 | CrO$_3$ (20 eq), DMP (22 eq), CH$_2$Cl$_2$, RT, 2 days | 43.2 | 80–90 (a) |
| 46 | CrO$_3$ (2.7 eq), DMP (2.7 eq), CH$_2$Cl$_2$, RT, 3 days | 20.4 | 80–90 (a) |
| 47 | CrO$_3$ (10 eq), DMP (11 eq), CH$_2$Cl$_2$, RT, 7 days | 250.0 | 68 (b,c) |
| 48 | CrO$_3$ (20 eq), DMP (22 eq), CH$_2$Cl$_2$, RT, 5 eq CrO$_3$-DMP complex added after 1 hr of rxn, 2 days | 100.9 | 80–90 (a) |
| 49 | CrO$_3$ (3 eq), DMP (3 eq), CH$_2$Cl$_2$, RT, 3 eq CrO$_3$-DMP complex added after 23 hrs of rxn, 26 hrs | 103.2 | 80–90 (a) | sm: starting material
a: yield based on nmi of crude product
b: yield based on isolated pure product
c: side products were formed

TABLE 5

| Example | Reagents and Conditions | | Notes |
|---|---|---|---|
| 50 | R = Ac | CH$_3$Li (15 eq), THF, −89° C., ca 2h | a |
| 51 | R = Ac | H$_2$NNH$_2$, H$_2$O, 95% EtOH, 13h | (4) and (5)(b) |
| 52 | R = Ac | H$_2$NNH$_2$, H$_2$O, 95% EtOH, 20h | (4) and (5)(b) |
| 53 | R = Ac | n-BuLi (6 eq), THF, −89° C., ca 2h | (6)(c) |
| 54 | R = Ac | H$_2$NNH$_2$, MeOH, H$_2$O, 3 days | (4) and (5)(b) |
| 55 | R = Ac | NH$_3$, H$_2$O, MeOH, H$_2$O, 4 days | Decomposed |
| 56 | R = Ac | NHMe$_2$, MeOH, H$_2$O, 20h | Decomposed |
| 57 | R = Ac | NMe$_3$, MeOH, H$_2$O, 20h | Decomposed |
| 58 | R = Ac | NaHCO$_3$, MeOH, 3 days at RT, 3.5h at 50° C. | Decomposed |
| 59 | R = Ac | NHEt$_2$, MeOH, H$_2$O, ca 20h | Decomposed |
| 60 | R = Ac | H$_2$NNHCOPh, MeOH, 2 days at RT, ca 5h at 50° C. | No reaction |
| 61 | R = Ac | DMAP, MeOH, ca 2 days at 50° C. | No reaction |
| 62 | R = Ac | NaHCO$_3$, H$_2$O$_2$, THF, 3 days at RT | No reaction |
| 63 | R = Ac | H$_2$NNH$_2$, MeOH, ca 26h | Complicated |
| 64 | R = Ac | n-BuLi (6 eq), THF, −89° C., ca 0.5h | (6)(c) |
| 65 | R = Ac | n-BuLi (6 eq), THF, −40 to −45° C., ca 1h | (6)(c) |
| 66 | R = Ac | n-BuLi (6 eq), CH$_2$Cl$_2$, −40 to −45° C., ca 5h | Complicated |
| 67 | R = Ac | LiOh, H$_2$O$_2$, THF, 20h at RT | (5)(d) |
| 68 | R = Ac | sec-BuLi (20 eq), THF, −40 to −45° C., at 0.5, 1 day at rt | No reaction |
| 69 | R = Ac | n-BuLi (3 eq), THF, −40 to −45° C., ca 5h | Complicated |
| 70 | R = Ac | n-BuOLi (10 eq), THF, −40 to −45° C., ca 6h | Complicated |
| 71 | R = Ac | H$_2$NNH$_2$, MeOH, ca 26h at 50–55° C. | Decomposed |
| 72 | R = Ac | LiOH, H$_2$O$_2$, THF, 20h at RT | (5)(d) |
| 73 | R = Ac | H$_2$NNH$_2$, THF, ca 26h at RT | Decomposed |
| 74 | R = Ac | H$_2$NNH$_2$, 95% EtOH, 50–55° C., 24h | Decomposed |
| 75 | R = Ac | n-BuLi (6 eq), THF, −40 to −50° C., ca 0.5h | (5)(d) | a: complicated product, reagent (CH$_3$Li) was not titrated
b: complicated products containing (5) as a major one and minor (6) plus other unknown products
c: compound (4) as a major product plus other unknown products
d: compound (5) as a major one, n-Butyllithium was not titrated

TABLE 6

| Example | Amount of 7.13-DABIII (mg) | Reagents and Solvent | Conditions | Products (Yield) |
|---|---|---|---|---|
| 76 | 9.1 | HMH, 95% EtOH | room temperature, 25.5 hours | a(55.4%) b(27.0%) plus 1 by-product |
| 77 | 1.9 of a | HMH, 95% EtOH | room temperature, 71 hours | starting material |
| 78 | 15.1 | HMH, 95% EtOH | room temperature, 72.5 hours | a(53.0%) b(18.0%) plus 1 by-product |
| 79 | 2.4 | HMH, 95% EtOH | 45–50° C., 23.5 hours | a(50.0%) b(49.4%) plus 1 by-product |
| 80 | 10.8 | DIBAL, dry THF | −78° C. room temperature, 22 hours | b(42.5%) c(20.2%) plus 1 by-product |
| 81 | 5.6 | HMH dry THF | room temperature 30 hours | 6.5 mg of crude a starting material |
| 82 | 6.1 | Anhydrous hydraxine, | room temperature 30 hours | 7.1 mg of crude a starting material |
| 83 | 7.0 | HMH 0.75 eq. DMAP, 95% EtOH | room temperature 50 hours | b(42.0%) plus 2 by-products |
| 84 | 25.0 | HMH 0.5 eq. DMAP 95% EtOH | room temperature 48.5 hours | a(37.0%) b(34.9%) plus 1 by-product |
| 85 | 20.6 | HMH 0.5 eq. DMAP 95% EtOH | 40° C., 22 hours | decomposition |
| 86 | 19.9 | HMH 0.75 eq. DMAP 95% EtOH | room temperature 69 hours | a(17.8%) b(26.6%) plus 2 by-products[1,2] |
| 87 | 20.6 | HMH 2.5 eq. DMAP 95% EtOH | room temperature 22 hours | a(11.7%) b(22.1%) plus 3 by-products[2] |
| 88 | 5.8 | HMH 2.5 eq. DMAP 95% EtOH | 0—4° C. 334 hours | 7.4 mg crude a(major) b(minor) |
| 89 | 5.8 | HMH 2.5 eq. DMAP 95% EtOH | room temperature 73 hours | a(33.5%) b(65.8%) plus 1 by-product[2] |
| 90 | 6.4 | HMH 2.5 eq. DMAP 95% EtOH | room temperature 75 hours | a(82.5%) b(38.5%) plus 1 by-product[2] |
| 91 | 4.7 of b | HMH 2.5 eq. DMAP 95% EtOH | room temperature 187 hours | 3.9 mg of crude starting material plus 3 other products[1,2] |
| 92 | 6.9 | HMH 5 eq. Pyridine 95% EtOH | room temperature 70 hours | a(36.4%) b(57.0%) plus 1 by-product[2] |
| 93 | 5.7 | HMH 2.5 eq. DMAP 95% EtOH | 7° C., 335 hours | 7.6 mg of crude a(minor) b(major) plus 2 by-products[1,2] |
| 94 | 3.7 | HMH 2.5 eq. Imidazole 95% EtOH | room temperature 70 hours | 3.5 mg of crude a(minor) b(major) plus 2 by-products[1,2] |
| 95 | 3.6 | HMH 2.5 eq. Diisopropylamine 95% EtOH | room temperature 70 hours | 3.6 mg of crude a(very minor) b(major) plus 2 by-products[1,2] |
| 96 | 3.3 | HMH 2.5 eq. collidine 95% EtOH | room temperature 71 hours | 4.2 mg of crude starting material (very minor) a(major) b(minor) plus 2 by-products[1,2] |
| 97 | 3.5 | HMH 2.5 eq. TEA 95% EtOH | room temperature 71 hours | 3.7 mg of crude starting material (very minor) a(major) b(minor) |

TABLE 6-continued

| Example | Amount of 7.13-DABIII (mg) | Reagents and Solvent | Conditions | Products (Yield) |
|---|---|---|---|---|
| 98 | 3.3 | HMH 2.5 eq. N-methylmorpholine 95% EtOH | room temperature 71.5 hours | plus 2 by-products (major)[1,2] 3.9 mg of crude starting material (minor) a(major) b(minor) |
| 99 | 3.8 | HMH 2.5 eq. 3-Quinuclidinol 95% EtOH | room temperature 72 hours | plus 2 by-products[1,2] 4.3 mg of crude starting material (major) a(major) b(minor) |
| 100 | 2.7 | HMH 2.5 eq. Imidazole 95% EtOH | room temperature 23.5 hours | plus 1 by-products[1] 2.7 mg of crude a(minor) b(major) |
| 101 | 2.7 | HMH 2.5 eq. Diisopropylamine 95% EtOH | room temperature 23 hours | plus 1 by-product (major)[2] 3.7 mg of crude a(minor) b(major) |
| 102 | 3.7 | HMH 2.5 eq. Diisopropylamine acetontrile | room temperature 25 hours | plus 2 by-products (major)[2] 4.1 mg of crude a(minor) b(major) |
| 103 | 3.4 | HMH 2.5 eq. Diisopropylamine DMG | room temperature 25 hours | plus 3 by-products[1,2] 3.6 mg of crude a(minor) b(major) |
| 104 | 3.7 | HMH 2.5 eq. Diisopropylamine DMSO | room temperature 25.5 hours | plus 3 by-products[1,2] 4.8 mg of crude a(minor) b(major) |
| 105 | 3.6 | HMH 2.5 eq. Diisopropylamine HMPA | room temperature 25.5 hours | plus 3 by-products[1,2] 5.0 mg of crude a(minor) b(major) |
| 106 | 4.5 | HMH 2.5 eq. Diisopropylamine MEOH | room temperature 197 hours | plus 3 by-products[1,2] 4.6 mg of crude b plus 3 by-products |
| 107 | 3.6 | HMH 2.5 eq. Diisopropylamine iso-Butanol | room temperature 197 hours | 4.2 mg of crude b plus 3 by-products |
| 108 | 4.5 | HMH 2.5 eq. DMAP 95% EtOH | 7° C., 141.5 hours | 4.2 mg of crude virtually no a b(major) plus 2 by-products (minor) |
| 109 | 5.0 | HMH 2.5 eq. Imidazole 95% EtOH | 7° C., 141.5 hours | 5.4 mg of crude virtually no a b(major) plus 2 by-products (minor) |
| 110 | 4.7 | HMH 2.5 eq. Diisopropylamine 95% EtOH | 7° C., 142 hours | 4.2 mg of crude virtually no a b(major) plus 2 by-products (minor) |
| 111 | 4.5 | HMH 2.5 eq. DMAP 95% EtOH | 4° C., 42 hours | a b |
| 112 | 4.7 | HMH 2.5 eq. Imidazole 95% EtOH | 4° C., 42 hours | a b |

HMH: hydrazine monohydrate
a: C-10 group is OH, C-13 group is OAc in product (5)
b: C-10 group is OH, C-13 group is OH in product (4), which is DAB-III
c: C-10 group is OAc, C-13 group is OH in product (6)

What is claimed is:

1. A method of converting 9-dihydro-13-acetylbaccatin III into 10-deacetylbaccatin III comprising the steps of:
    (a) protecting the C-7 group of 9-dihydro-13-acetylbaccatin III by replacing the C-7 hydroxyl group with a protecting group;
    (b) oxidizing the C-9 hydroxyl group in the resulting product to produce a C-9 ketone; and
    (c) deprotecting the C-9 ketone to form 10-deacetylbaccatin III.

2. The process of claim 1, wherein the 9-dihydro-13-acetylbaccatin III is reacted with a protecting reagent in the presence of a dry base to yield a C-7 protected 9-dihydro-13-acetylbaccatin III.

3. The process of claim 2, wherein the C-7 protected 9-dihydro-13-acetylbaccatin III is oxidized using a 3,5-disubstituted pyrazole and a metal oxide to produce the corresponding C-9 ketone.

4. The process of claim 3, wherein the C-9 ketone is deprotected by subjecting the C-9 ketone to hydrolysis using a reagent selected from the group consisting of an acid, a base and a strong nucleophile, selected from the group consisting of a bicarbonate, a carbonate, ammonia, an amine, a hydrazine, a hydroxide, a hydroperoxide and an aklyllithium.

5. The process of claim 1, wherein the C-7 hydroxyl group of 9-dihydro-13-acetylbaccatin III is replaced with an acetyl group to produce 9-dihydro-7,13-diacetylbaccatin III; the 9-dihydro-7,13-diacetylbaccatin III is oxidized to yield 7,13-diacetylbaccatin III; and the 7,13-diacetylbaccatin III is deprotected to produce 10-deacetylbaccatin III.

6. The process of claim 5, wherein the 9-dihydro-13-acetylbaccatin III is reacted with acetic anhydride in the presence of pyridine and p-N,N-dimethylaminopyridine to produce 9-dihydro-7,13-diacetylbaccatin III.

7. The process of claim 6, wherein the 9-dihydro-7,13-diacetylbaccatin III is oxidized using a 3,5-distributed pyrazole with a chromium oxide oxidant.

8. The process of claim 7, wherein the 3,5-disubstituted pyrazole is 3,5-dimethylpyrazole, and the oxidant is chromium trioxide.

* * * * *